United States Patent

Platz et al.

[11] Patent Number: 5,919,935
[45] Date of Patent: Jul. 6, 1999

[54] PSORALEN SENSITIZERS FOR VIRAL INACTIVATION

[75] Inventors: Matthew S. Platz, Columbus, Ohio; Tongqian Chen, Fort Collins, Colo.; Shashi S. Kagan, Valley Cottage, N.Y.; Helena M. Pereira, Aubervilliers, France

[73] Assignee: The Ohio State Research Foundation, Columbus, Ohio

[21] Appl. No.: 08/975,753

[22] Filed: Nov. 21, 1997

Related U.S. Application Data

[60] Provisional application No. 60/033,088, Nov. 22, 1996.
[51] Int. Cl.$^6$ .................................................. C07D 405/12
[52] U.S. Cl. ........................ 546/283.1; 549/282; 548/526
[58] Field of Search ........................ 546/283.1; 549/282; 548/526

[56] References Cited

U.S. PATENT DOCUMENTS

| | | | |
|---|---|---|---|
| 5,342,752 | 8/1994 | Platz et al. | 514/297 |
| 5,418,130 | 5/1995 | Platz et al. | 435/2 |
| 5,587,490 | 12/1996 | Goodrich et al. | 549/282 |

OTHER PUBLICATIONS

"The design and development of selective photoactivated drugs for sterilization of blood products", by Goodrich, et al., *Drugs of the Future*, 1997, 22(2), pp. 159–171.

"Electron Transfer Chemistry of Psoralen and Coumarin Derivatives by Means of Radiolytic and Electrochemical Experiments", by Chen, et al., *J. Phys. Chem. A.*, vol. 101, No. 11, 1997, pp. 2124–2130.

"New Psoralen Derivatives for Selective Viral Inactivation in Platelet Concentrates", by Platz, et al., *The Spectrum*, Fall 1995, vol. 8, Issue 3, pp. 11–20.

"Synthesis, Evaluation and Mechanistic Studies of Halogenated Psoralen and Acridine Photosensitizers: A Dissertation", by Tongqian Chen, 1995.

*Primary Examiner*—Jane Fan
*Attorney, Agent, or Firm*—Calfee, Halter & Griswold LLP

[57] ABSTRACT

The present invention relates to novel, halogenated psoralen compounds that are useful for inactivating vital contaminants in blood-derived products, particularly blood-derived products that contain platelets or red blood cells. The psoralen compounds of the present invention have the following formula:

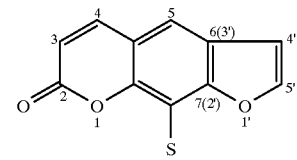

The side chain S which is a attached to the carbon at position 8 of the psoralen moiety contains a quartemary ammonium group which comprises a central nitrogen atom, a linking group L, and an aromatic ring structure. The linking group L joins the central nitrogen atom of the quartemary ammonium group to the psoralen moiety. The linking group L comprises a carbon chain having 2 to 12 carbon atoms and an oxygen atom which links the carbon chain to the psoralen moiety. The psoralen compounds of the present invention also comprise one or more halogens attached to the psoralen moiety. Preferably the halogens are attached to the carbon atom at position 3 or 5 of the psoralen moiety. In one class of these novel psoralen compounds, the central nitrogen atom of the quartemary ammonium group is a component of the aromatic ring structure. In another class, the central nitrogen atom is attached to three substituent groups, $R^1$, $R^2$, and $R^3$ wherein $R^3$ has the following structure: —$R^5$—CH=CH—$R^6$ wherein $R^5$ is a carbon chain comprising 1 to 3 carbon atoms, and wherein $R^6$ is the aromatic ring, The present invention also relates to methods of making and using the novel psoralen compounds.

10 Claims, 3 Drawing Sheets

BCP     BPP

PSORALEN SENSITIZERS FOR VIRAL INACTIVATION

This application claims the benefit of U.S. Provisional application(s) No(s).: application Ser. No. 60/033,088, filing date Nov. 22, 1996.

Blood-derived products that are used as lab reagents, such as serum, or that are injected into patients, such as platelet concentrates or purified plasma protein fractions, can be contaminated with viruses and other microbial contaminants. Certain known psoralen compounds such as 8-methoxy psoralen (8-MOP) and 4-5-8-trimethylpsoralen (AMT) are capable of inactivating viruses in blood-derived products. Upon photolysis, 8-MOP and AMT undergo cycloaddition reactions with nucleic acids, proteins and unsaturated lipids. They also sensitize the formation of active oxygen species. These reactions can kill bacteria and inactivate viruses.

Unfortunately, all of the currently known psoralens cause unacceptable damage to platelet membranes. Accordingly, it is desirable to have new psoralen compounds that overcome the disadvantages of the currently available psoralens. New psoralen compounds that selectively damage nucleic acids and cause fewer side reactions, such as damage to platelet membranes, are especially desirable.

SUMMARY OF THE INVENTION

The present invention relates to novel, halogenated psoralen compounds that are useful for inactivating vital contaminants in blood-derived products, particularly blood-derived products that contain platelets or red blood cells. The psoralen compounds of the present invention have the following formula:

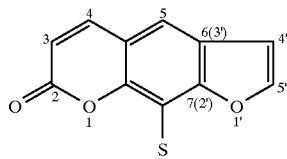

The side chain S which is a attached to the carbon at position 8 of the psoralen moiety contains a quarternary ammonium group which comprises a central nitrogen atom, a linking group L, and an aromatic ring structure. The linking group L joins the central nitrogen atom of the quartenary ammonium group to the psoralen moiety. The linking group L comprises a carbon chain having 2 to 12 carbon atoms and an oxygen atom which links the carbon chain to the psoralen moiety. The psoralen compounds of the present invention also comprise one or more halogens attached to the psoralen moiety. Preferably the halogens are attached to the carbon atom at position 3 or 5 of the psoralen moiety.

In one class of these novel psoralen compounds, the central nitrogen atom of the quarternary ammonium group is a component of the aromatic ring structure. Preferably, the aromatic ring is a pyridine or substituted pyridine. In a preferred embodiment of this class, the psoralen compound is 5-bromo-8{3-[(4-methoxycarbonyl)pyridinio]propyloxy}psoralen bromide (BPP).

In another class of the novel psoralen compounds, the S side chain has the structure shown below:

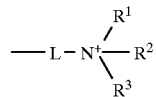

In this class of compounds, the central nitrogen atom is attached to three substituent groups, $R^1$, $R^2$, and $R^3$ wherein $R^3$ has the following structure

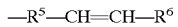

wherein $R^5$ is a carbon chain comprising 1 to 3 carbon atoms, and wherein $R^6$ is the aromatic ring,. In a preferred embodiment of this class, the psoralen compound is 5-bromo-8-[(3-cinnamyldiethylammonio)propyloxy]psoralen bromide (BCP).

The present invention also relates to methods of making and using the novel psoralen compounds.

DETAILED DESCRIPTION OF THE INVENTION

Figure 1:
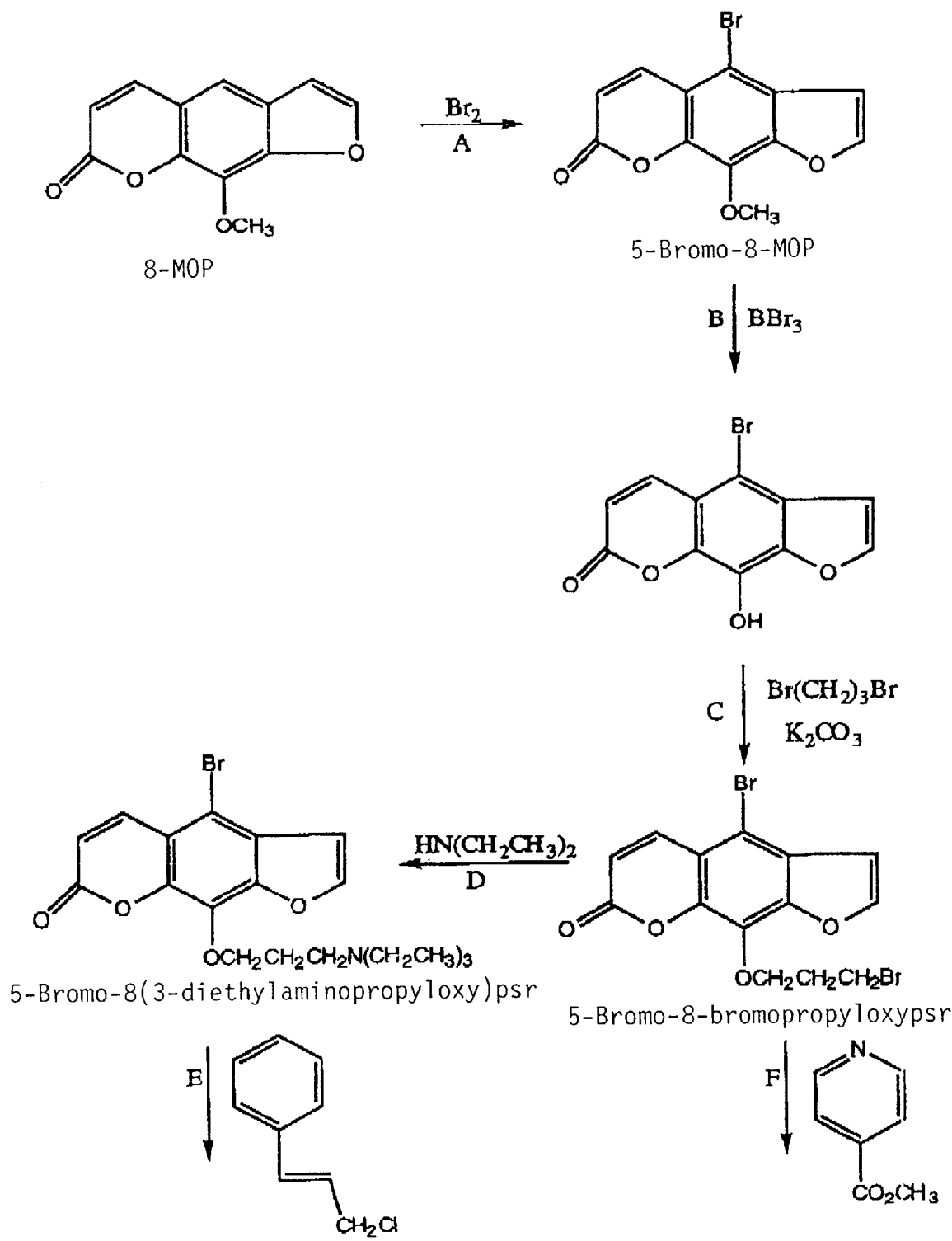
FIG. 1 is a representations of the steps used to prepare the novel halogenated compounds 5-bromo-8-[(3-cinnamyldiethylammonio)propyloxy]psoralen bromide (BCP) and 5-bromo-8{3-[(4-methoxycarbonyl)pyridinio]propyloxy}psoralen bromide (BPP).
Figure 1:
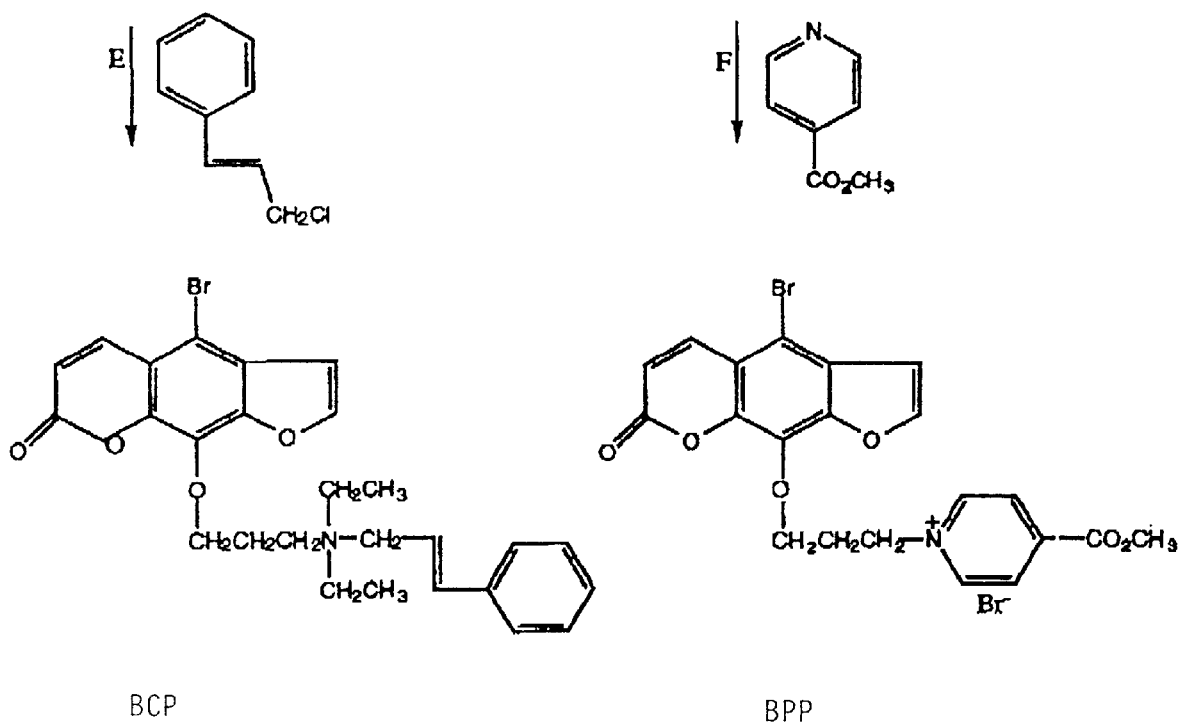
Figure 2:
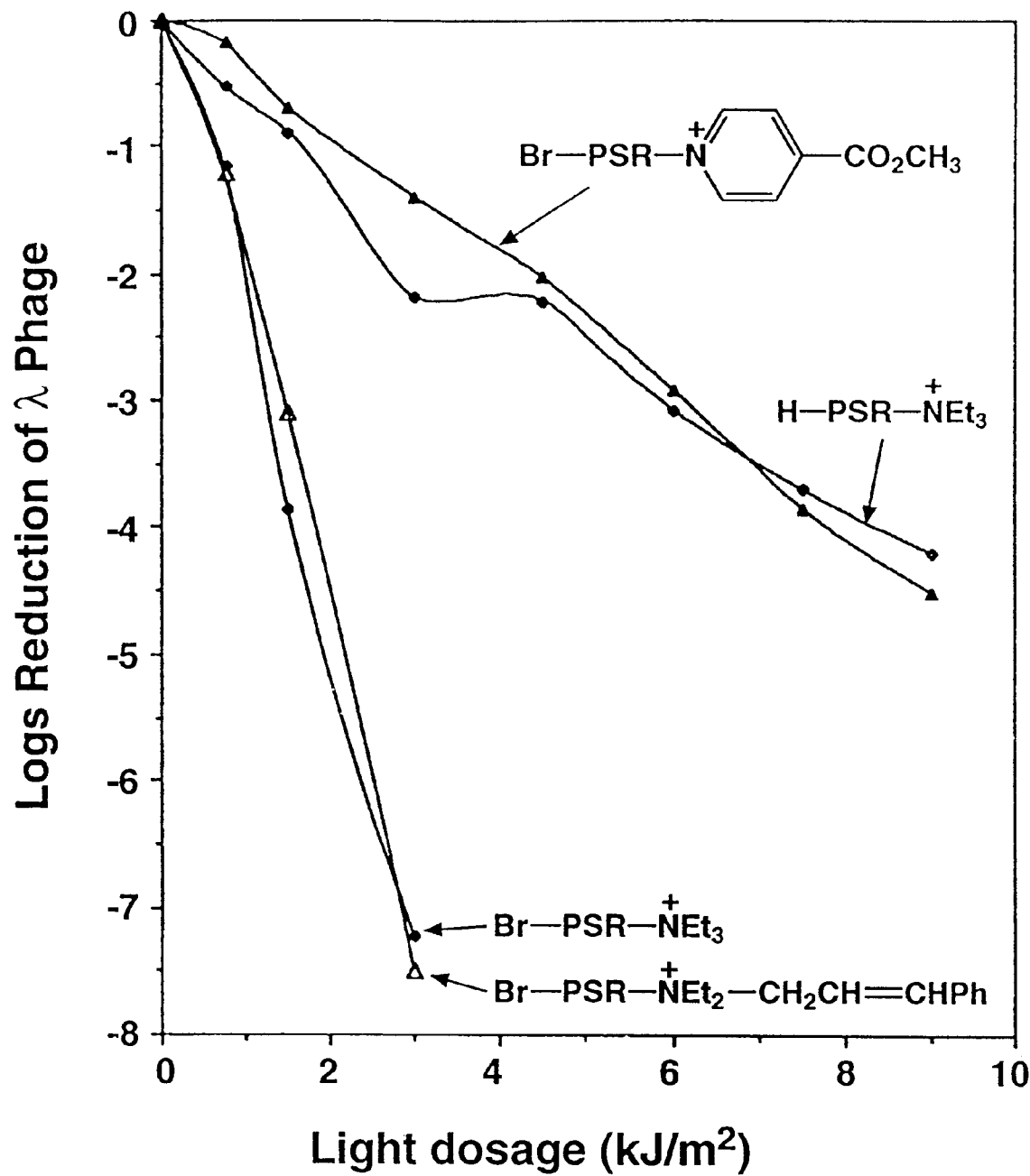
FIG. 2 shows the decrease in virus titer when the virus bacteriophage lambda is inactivated with the novel psoralen compounds BCP and BPP of the present invention and with the conventional psoralen compounds 5-bromo 8-[(3-ethylammonio propyloxy] psoralen (BEP) and 8-[(3-ethylammonio propyloxy] psoralen (HEP).

The present invention relates to novel, halogenated psoralen compounds having the following formula:

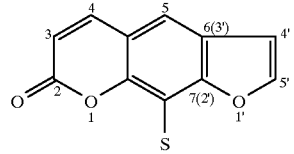

The side chain S which is a attached to the carbon at position 8 of the psoralen moiety contains a quarternary ammonium group which comprises a central nitrogen atom, a linking group L, and an aromatic ring structure. The linking group L joins the central nitrogen atom of the quartenary ammonium group to the psoralen moiety. The linking group L comprises a carbon chain having 2 to 12, preferably 3 to 8 carbon atoms, and an oxygen atom which links the carbon chain to the psoralen moiety. Preferably the carbon chain is aliphatic.

In one class of the novel psoralen compounds, the central nitrogen atom of the quarternary ammonium group is a component of the aromatic ring structure. Preferably, the aromatic ring of this embodiment is a pyridine. More preferably, an $R^2$ group is attached to the aromatic ring, wherein the $R^2$ group is an alkyl, ester, amide, cyano, halogen, nitro or —O—C(O)—$R^3$, wherein $R^3$ is a carbon chain having 1 to 10 carbons. Preferably the $R^2$ group is attached to the aromatic ring at the ortho, meta, or para position or a combination thereof. In a preferred embodiment of this class, the psoralen compound is 5-bromo-8{3-[(4-methoxycarbonyl)pyridinio]propyloxy}psoralen bromide (BPP).

In another class of the psoralen compounds, the S side chain is as follows:

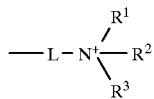

In this class of compounds, the central nitrogen atom is attached to three substituent groups, $R^1$, $R^2$, and $R^3$ wherein $R^3$ has the following structure:

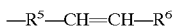

wherein $R^5$ is a carbon chain comprising 1 to 3 carbon atoms, and wherein $R^6$ is the aromatic ring, Preferably, $R^6$ is a simple phenyl group or substituted phenyl group. Preferably, the substituent groups $R^1$ and $R^2$ are aliphatic chains having 1 to 8 carbon atoms, more preferably 2 to 6 carbon atoms. In a preferred embodiment of this class, the psoralen compound is 5-bromo-8-[(3-cinnamyldiethylammonio)propyloxy]psoralen bromide (BCP).

The psoralen compounds of the present invention also comprise one or more halogens, preferably bromine, attached to the psoralen moiety. Preferably, the halogen is attached to the carbon atom at position 3 or at position 5 of the psoralen moiety. Preferably, the psoralen compounds of the present invention have an average molecular weight of 1000 or less, more preferably from 200 to 400.

Certain conventional psoralen compounds such as 8-MOP, and AMT, and HEP are all able to completely inactivate the virus, bacteriophage Φ6, in platelet concentrates under normal oxygen tension. Margolis-Nurono et al. (1992) Transfusion 32, 51; Platz et al. The Spectrum (1995) 8(3): 11–20. Unfortunately, such treatment also causes unacceptable damage to the platelet membrane. This damage is oxygen dependent and obviated by addition of quenching agents, such as mannitol, to the platelet concentrates. Accordingly, it is believed that photolysis of 8-MOP, AMT, and HEP, all of which accumulate in the platelet membranes as well as in the nucleic acids of the viral contaminant, results in the formation of an excited triplet state that reacts with molecular oxygen in the platelet concentrates to form singlet oxygen. It is the singlet oxygen which ultimately induces the lethal membrane damage.

The novel halogenated psoralen compounds of the present invention do not bind to platelet membranes to the same extent as the conventional psoralen compounds 8-MOP, AMT or HEP. The photolysis of the novel psoralen compounds does not result in the production of an excited triplet state. Accordingly, it is believed that the novel psoralen compounds produce less singlet oxygen and cause less damage to platelets than the conventional psoralen compounds. Thus, the novel psoralen compounds will be especially advantageous for inactivating viruses in blood-derived products that contain platelets or red blood cells such as, for example, platelet concentrates and units of packed red cells.

Using the Novel Psoralen Compounds

To inactivate viruses or other vital contaminants in blood-derived products, one or more of the novel psoralen compounds are added to the blood-derived product, which preferably is in a liquid state, and the blood-derived product-psoralen mixture is then exposed to electromagnetic radiation of sufficient wavelength and intensity for a time sufficient to activate the psoralen compounds contained in the mixture. When the novel halogenated psoralen compounds are used to inactivate viruses in lyophilized blood derived products such as, for example, lyophilized plasma, it is preferred that the psoralen compounds be activated by exposure to X-ray. When the novel halogenated psoralen compounds are used to inactivate viruses in blood-derived products that contain platelets or red blood cells, it is preferred that ultraviolet light, more preferably ultraviolet light at a wavelength of 400 nanometers or less, be used.

The novel psoralen compounds bind to nucleic acids by intercalation at a site comprising a single guanine base. Absorption of a WVA photon by the psoralen in the presence of guanine leads to electron transfer and the formation of free radicals and ultimately nucleic acid cleavage and viral death. Specific methods of using halogenated psoralens to inactivate viruses in lyophilized and hydrated plasma, packed platelets, platelet concentrates, packed red blood cells, and serum, particularly fetal bovine serum are described in U.S. Pat. No. 5,418,130 issued on May 23, 1995, to Platz et al, which is specifically incorporated herein by reference.

Making the Novel Psoralen Compounds

The following methods for making a representative example of each class of the novel halogenated psoralen compounds of the present invention using the method depicted in FIG. 1 are for purposes of illustration only and are not intended to limit the scope of the appended claims. Example 1: 5-bromo-8-[(3-cinnamyldiethylammonio) propyloxy]psoralen bromide (BCP)

A. Synthesis of 5-bromo-8-methoxypsoralen 8-methoxypsoralen (4.32 g, 20.0 mmol), obtained from Aldrich Chemical Company was dissolved in tetrahydrofuran (50 mL). To the mixture was added dropwise, with stirring, elemental bromine (4.0 g, 25 mmol) over 20 min at room temperature. The reaction mixture turned red when bromine was added. Precipitate appeared in 5 min. Extra bromine was consumed by solvent tetrahydrofuran in an extended 2 hr stirring or by the addition of 10% sodium thiosulfate solution. The crude product was collected by filtration and was purified with recrystallization from ethanol to give the product 5-bromo-8-methoxypsoralen (5.38 g, 91% yield) as a white solid. mp 178–80° C. $^1$H—NMR (DMSO(dimethylsulfoxide)—d$_6$, ppm): 8.22(d, J=2.2 Hz, 1H), 8.11 (d, J=9.9 Hz, 1H),7.01(d,J=2.2 Hz, 1H),6.53(d, J=9.9 Hz, 1H),4.17(s,3H).

B. Synthesis of 5-bromo-8-hydroxypsoralen

Boron tribromide in hexane (5.1 mL, 5 mmol) was added to a solution of 5-bromo-8-methoxypsoralen (0.70 g, 2.4 mmol) in dry methylene chloride (50 mL). The resulting reaction mixture was stirred at room temperature for 7 h after which some yellow solid precipitated. Water (2 mL) was added cautiously, causing an exotherm, which subsided after a few minutes. Additionally water (125 mL) was added, and the heterogeneous mixture was stirred at RT overnight. The crude product was collected by vacuum filtration and air dried. The crude product was recrystallized from acetonitrile (45 mL) to give the product 5-bromo-8-hydroxypsoralen (0.40 g, 1.43 mmol, 58% yield); m.p. 254–256° C. $^1$H—NMR (dimethylsulfoxide [DMSO]—d.)δ. 6.5 (d, IH), 7.0(s, IH), 8.1–8.2(ds, 2H), 10.8–11.1(broad, alcohol—H).

C. Synthesis of 5-bromo-8-((ω-bromopropyloxy)psoralen

5-Bromo-8-hydroxypsoralen (0.35 g, 1.22 mmol) was dissolved in anhydrous acetone (100 ml). 1,3-Dibromoprosane (1.5 mL) and anhydrous $K_2CO_3$ (3.0 g) were added. The resulting mixture was refluxed for 48 hours. After cooling, the acetone solution was filtered and the solid residue was washed twice with acetone (950 mL). The combined acetone solutions were concentrated to yield an oil, which was dissolved in benzene (150 mL). This was chromatographed through a silica gel column containing water (5%). The product eluted with benzene was concentrated to give a white solid. This was recrystallized from benzene: hexane (1:5) to give the product, 5-bromo-8-(ω-bromopropyloxy)psoralen (0.30 g, 0.73 mmol, 60% yield): m.p. 94–98° C. $^1$H—NMR (DMSO—$d_2$)δ:2.20–2.30 (m.2H), 3.75 (t,2H), 4.5 (1, 2H), 6.5 (d, IH), 7.05 (s, IH), 8.15 (d, IH), 8.25 (s, IH).

D. Synthesis of 5-bromo-8-(3-diethylaminopropyloxy) psoralen

5-Bromo-8(o-bromopropyloxy)psoralen (0.30 g, 0.73 mmol) was dissolved in anhydrous ethanol (10 mL). Diethylamine (2 mL) was added and heated at 65° C. for 5 h. After cooling, the brown solution was poured into water (100 mL) and extracted twice with chloroform (200 mL). The organic layer was dried with $MgSO_4$ and concentrated to give an oil. The hydrochloride salt of the product was precipitated by adding anhydrous ethanol (2 mL), concentrated aqueous HCl (0.5 mL) and ether (2 mL). The resulting mixture was cooled in the freezer overnight and vacuum filtered to give a white solid that was recrystallized from anhydrous ethanol: hexane (1:5) to give the salt (0.15 g, 0.35 mmol, 48% yield); m.p. 196–198° C. $^1$H—NMR ($D_3$O/DMSO—$d_4$)δ0–0.1 (t, 6H)$_7$ 0.8–0.95 (m, 2H), 1.9–2.05 (q, 4H), 2.1–2.2 (m, 2H), 3.15(t, 2H), 5.0 (d, IH), 5.5 (s, IH), 6.5(d, IH) 6.6(s, IH) —$^{13}$C—NMR (DMSO)δ8.36, 23.84, 46.18, 47.60, 71.03, 105.63, 107.16, 115.40, 116.07, 127.34, 130.29, 142.48, 143.68, 146.33, 148.82, 158.96. Fast atom bombardment (FAB) mass spectrum, m/e 396 (M+I)$^+$, calculated ($C_{18}O_4NBrH_{20}$) m/e 395.

E. Synthesis of product 5-bromo-8-[(3-cinnamyldiethylammonio)propyloxy]psoralen bromide Crude 5-bromo-8-(3-diethylaminopropyloxy)psoralen (0.91 g) was dissolved in acetonitrile. To this was added cinnamyl bromide (2.0 mL), and anhydrous potassium carbonate (0.5 g). The resulting mixture was stirred under argon (50° C., 48 hr). The potassium carbonate residue was removed by filtration and washed with hot acetonitrile. The combined filtrate was then evaporated under reduced pressure to give a white solid. The crude product was recrystallized from ethanol and ethyl acetate to give the product 5-bromo-8-[(3-cinnamyldiethylamnionio)propyloxy] psoralen bromide (0.674 g, 57% yield) as a white solid. $^1$H—MNR (DMSO(dimethylsulfoxide)—$d_6$, ppm): 8.29 (d, J=2.3Hz, 1H), 8.27 (d, J=9.7Hz, 1H), 7.20 (d, J=2.3Hz, 1H), 6.62 (d, J=9.7Hz, 1H), 4.51 (t, J=5.6Hz, 2H), 3.52–3.42 (m, 2H), 3.32 (q, J=7.1Hz, 6H), 2.23–2.13 (m, 2H), 1.24 (t, J=7.1Hz, 9H). MS (m/e, intensity %): 513 (18.46, M+3$^+$), 512 (66.86, M+2$^+$), 511 (19.96, M+1$^+$), 510 (64.19, M+), 394 (28.40) 392 (25.44), 117 (100).

The structure of BCP is as follows:

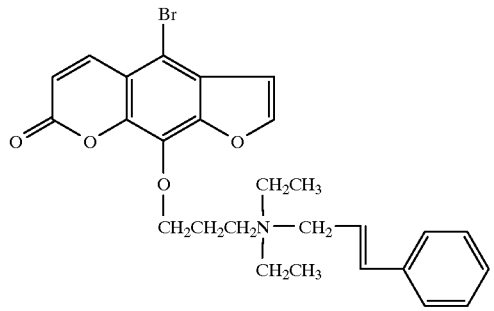

Example 2 5-bromo-8 {3[(4-methoxycarbonyl)pyridinio]propyloxy}psoralen bromide (BPP)

5-Bromo-8-(3-bromopropyloxy)psoralen 0.804 g, (2.00 mmol), prepared as described above in example 1 was dissolved in distilled methyl isonicotinate (5 mL). The mixture was then stirred under argon (50° C., 18 hr). A grey precipitate was formed and ethyl acetate (20 mL) was added to ensure complete precipitation of the product. The grey solid was separated by filtration and recrystallized from ethanol and ethyl acetate to give the product 5-bromo-8{3-[(4-methoxycarbonyl)pyridinio]propyloxy}psoralen bromide (0.887 g, 82% yield) appearing as yellow crystals. mp. 192–5° C. (dec.). HMNR (DMSO—$d_6$, ppm): 9.45 (d, J=6.5Hz, 2H), 8.53 (d, J=6.5Hz, 2H), 8.29 (d, J=2.2 Hz, 1H), 8.17 (d, J=9.9Hz, 1H), 7.08 (d, J=2.2Hz, 1H), 6.58 (d, J=9.9Hz, 1H), 5.04 (t, J=6.4Hz, 2H), 4.58 (t, J=5.5Hz, 2H), 3.99 (s, 3H), 2.59–2.52 (m, 2H). CNMR (DMSO—$d_6$, ppm): 162.6, 159.0, 148.8, 146.7, 145.7, 143.8, 143.0, 142.4, 130.0, 127.4, 127.1, 116.0, 115.1, 107.0, 105.3, 70.7,59.2, 53.8, 30.8, MS (m/e, intensity %): 461 (31.04, M+3$^+$), 460 (100, M+2$^+$), 459(31.27,M+1$^+$), 458(99.79,M+), 178 (28.11),151(37.59).

The structure of BPP is as follows:

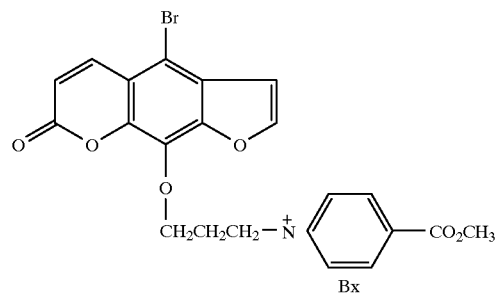

The DNA binding constants, photophysical characteristics, and ability to cleave DNA of the novel psoralen compounds BCP and BPP and the comparative psoralen compounds BEP and HEP which do not have an aromatic ring in the side chain were determined and compared.

Binding to DNA

The DNA binding constants ($K_{DNA}$) of BCP and BPP were determined by incubating solutions containing various concentrations of BCP or BPP with calf thymus DNA and ethidium bromide, measuring the decrease in fluorescence of the ethidium bromide at each concentration of BPP or BCP, plotting the relative fluorescence intensities (I./II) against the concentration and then calculating the intrinsic binding constant from the slope of the line so obtained. The intrinsic binding constants of two conventional psoralen compounds whose side chains lack an aromatic ring, namely 5-bromo 8-[(3-ethylammonio propyloxy] psoralen (BEP) and 8-[(3-ethylammonio propyloxy] psoralen (HEP) were also determined using the same protocol.

Specifically, stock solutions of the psoralen derivatives, ethidium bromide, and calf thymus DNA were made in Tris-HCI buffer. The concentrations of ethidium bromide and calf thymus DNA in the stock solutions were determined spectrophotometrically by using the following extinction coefficients: ethidium bromide, $\epsilon_{480}=5860 M^{-1}cm^{-1}$ and calf thymus DNA, $\epsilon_{260}=6600 M^{-1}cm^{-1}$.

Using the above stock solutions, a series of 2 mL samples were made. The samples contained calf thymus DNA and ethidium bromide at a concentration of about 5 to 10 $\mu$M, and varying concentrations of BPP, BCP, BEP, and HEP. The samples were left in the dark to equilibrate at room temperature for at least 4 hours before the ethidium bromide fluorescence of the each sample ($\lambda_{ex}=545$ nm, $\lambda_{ex}=595$ nm) was determined.

The results, which are shown in Table 1 below, demonstrate that the novel psoralen compounds BCP and BPP are able to bind to calf thymus DNA to the same extent as the conventional psoralen compounds BEP and HEP.

TABLE 1

A comparison of the novel psoralen compounds BPP and BCP with the conventional psoralen compounds BEP and HEP.

| Psoralen | $K_{DNA}$ ($\times 10^3$ uc$^{-1}$) | $T_n{}^a$ ($\mu$m) | $\Delta$ logs V.I.$^b$ at 4 kJ/m$^2$ light dose (kJ/m$^2$) | $\Phi_F$ | $\Phi_T$ |
|---|---|---|---|---|---|
| BEP (Comparative) | 4.1 | 40 | >7 | 0.74 | 2.0 |
| BCP | 3.2 | 50 | >7 | 0.71 | 0 |
| BPP | 4.0 | 50 | 2.2 | 0.27 | 0 |
| HEP (Comparative) | 0.3 | >600 | 2.0 | 1.00$^c$ | 1.00$^c$ |

$^a$Total light influx was 49.2 kJ/m$^2$. $\lambda$ = 350 nm.
$^b$The initial viral titer is $10^7$ pfu. Light wavelength is 350 nm.
$^c$By definition, all other values in the column are relative, all values are ±0.05.

Photolysis of Supercoiled Plasmid DNA

The abilities of the novel psoralen compounds BCP and BPP and the conventional psoralen compounds BEP and HEP to damage DNA were compared using plasmid pBR322. pBR322 is a double-stranded closed circular E. coli plasmid DNA that normally exists in a supercoiled form. When the plasmid DNA is damage or nicked, the supercoiled form is converted to a circular form. To assess the ability of these psoralens to nick the supercoiled DNA, buffered solutions containing increasing concentrations of BCP, BPP, BEP and HEP were mixed with a constant amount of pBR322, the resulting mixtures irradiated, and the change in structure of the supercoiled DNA determined by gel electrophoresis. Specifically, solutions of BCP, BPP, BEP and HEP in Tris-HCl were mixed with supercoiled pBR322 at a final DNA concentration of 40 $\mu$g/mL The solutions were left to equilibrate in the dark for at least 2 hours before irradiation took place. All irradiations were conducted in a Rayonet reactor equipped with lamps emitting desired wavelength light in a cold room at 3° C. Aliquots (10 $\mu$L) of samples were removed at the desired time intervals and resolved for gel electrophoresis. The results are shown in Table 1 above.

As shown in Table 1, the minimum concentrations of the novel psoralen compounds BPP and BCP and the minimum concentration of the conventional psoralen compound BEP required to nick plasmid DNA pBR322 and convert it completely from the supercoiled to the circular form ($T_N$, ) are the same.

Formation of Excited Triplet State.

The relative fluorescence quantum (intensity) in buffer of the novel psoralen compounds BCP and BPP and the comparative psoralen compounds BEP and HEP were measured. In addition, the yield of long lived (microsecond) triplet ($\Phi_T$) psoralen was measured by the transient absorption of the triplet produced by laser flash photolysis. The results indicate that the fluorescence intensity of the novel psoralen compound BCP is equal to that of the comparative psoralen compound BEP. The fluorescence intensity of the novel psoralen compound BPP is reduced by 64% relative to the conventional comparative psoralen compound BEP indicating substantial deactivation of the excited singlet state, $S_1$. As shown in Table 1, the yield of long lived triplet ($\Phi_T$) for both of the novel psoralen compounds BCP and BPP is zero. These results indicate that little to no singlet oxygen is produced when BCP and BPP are irradiated in compositions containing lipid membranes. Thus, the membrane damage to platelets and red blood cells is diminished when these two novel psoralen compounds are employed to inactivate viruses in blood-derived products containing cells or platelets, as compared to the conventional psoralens BEP and HEP.

Inactivation of Virus with BCP and BPP

Individual 0.1 ml suspensions containing 6×10$^7$ plaque forming units (pfu) of bacteriophage lambda in Tris-HCl were separately added to tubes containing 50 $\mu$m of the novel psoralen compounds BCP and BPP and the conventional psoralen compounds BEP, and HEP in Tris-HCl. The resulting samples were incubated in the dark at 4° C. for about one hour. The samples were then exposed to UV radiation at a wavelength of 350 nm. Aliquots of the samples were then mixed with host bacteria and spread on nutrient agar. Following a normal growth period, the plates were assayed for plaques. The reduction in viral titer resulting from treatment of the bacteriophage lambda suspensions with the novel psoralens BCP and BPP and the conventional psoralens BEP and HEP, irradiated at various light dosages is shown in FIG. 4. The log decrease in infectious bacteriophage lambda that results from treatment of the suspension with the novel psoralens BCP and BPP and the conventional psoralens BEP and HEP and exposure to UV light at a light dosage of 4kJ/m2 is shown in Table 1. These results indicate that the novel psoralen compound BCP and the conventional psoralen compound BEP are able to inactivate to the model virus to the same extent. Thus BCP is a very potent viral inactivator. In addition, these results indicate that irradiation of the viral suspension following treatment with the novel psoralen BCP also results in inactivation of this model virus although to a lesser extent than with BPP. Accordingly, the novel psoralen BPP is more preferred for inactivating viruses in solutions that do not contain platelets or red blood cells. The results also indicate that the novel psoralen BPP is a more selective agent of viral inactivation than is the conventional psoralen BEP. It is believed that the conventional psoralen BEP inactivates $\lambda$ phage by damaging both DNA and protein whereas the damage sensitized by the novel psoralen BPP is more restricted to nucleic acids.

Accordingly, BPP is more preferred for inactivating viruses in solutions that contain platelets or red blood cells.

Other novel halogenated psoralen compounds wherein the S chain comprises a pyridine or substituted pyridine are prepared by providing a halogenated 8-bromoalkyloxypsoralen. Preferably, the halogen is attached to the carbon at position 3 or position 5 of the psoralen moiety. More preferably, the halogen is a bromine. The halogenated 8-bromoalkyloxy psoralen is then reacted with a pyridine or substituted pyridine comprising an R group that is an allyl, ester, amide, cyano, halogen, nitro or —O—C(O)—R³, wherein R³ is a carbon chain having 1 to 10 carbons to provide the final product.

Other novel halogenated psoralen compounds wherein the S chain has the formula

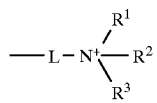

are prepared by providing an 8-bromoalkyloxy psoralen. The halogenated 8-bromoalkyloxy psoralen is then reacted an alkylamine comprising 1 to 8 carbon atoms to provide a halogenated 8-dialkylaminoalkyloxy psoralen. The dialkylamino alkyloxy psoralen is then reacted with a cinnamoyl halide to provide the final product.

While the invention has been described to some degree of particularity, various adaptations and modifications can be made without departing from the scope of the invention as defined in the appended claims.

What is claimed is:

1. A psoralen compound having the structure:

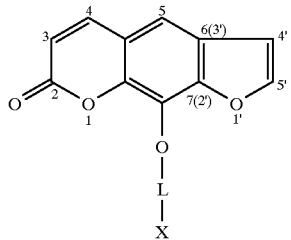

wherein L is a carbon chain having 2 to 12 carbon atoms;
wherein X is an aromatic moiety selected from the group consisting of
  a five-membered ring containing a nitrogen atom as a member of the ring and
  a six-membered ring containing a nitrogen atom as a member of the ring;
wherein the nitrogen atom of the aromatic moiety is the central nitrogen atom of a quartemary ammonium group;
wherein L attaches the aromatic moiety to the oxygen atom via the central nitrogen atom; and
wherein a halogen is attached to the structure at position 3, 4, 5, 6(3'), 4', 5', or 7(2').

2. The psoralen compound of claim 1, wherein L is a carbon chain having 3 to 8 carbon atoms.

3. The psoralen compound of claim 1, wherein the aromatic moiety is a six-membered ring.

4. The psoralen compound of claim 1,
wherein the aromatic moiety is a pyridine substituted with a an alkyl, an alkoxy carbonyl —C(O)NH₂, a cyano, a halogen, a nitro or —O—C(O)—R"
wherein R" is a carbon chain having 1 to 10 carbons.

5. A psoralen compound having the following structure:

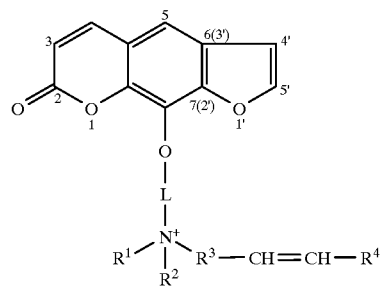

wherein L is a carbon chain having 2 to 12 carbon atoms
wherein R¹ and R² are aliphatic chains having 1 to 8 carbon atoms;
wherein R³ is a carbon chain having 1 to 3 carbon atoms;
wherein R⁴ is an aromatic ring; and
wherein a halogen is attached to the structure at position 3, 4, 5, 6(3'), 4', 5', or 7(2').

6. The psoralen compound of claim 5 wherein R⁴ is a phenyl group.

7. The psoralen compound of claim 1 wherein a bromine is attached to the carbon at position 3 or position 5 of the structure.

8. The psoralen compound of claim 3 wherein the psoralen compound is
5-bromo-8 {3-[(4-methoxycarbonyl)pyridinio] propyloxy}psoralen bromide.

9. The psoralen compound of claim 5 wherein the psoralen compound is 5-bromo-8-[(3-cinnamyldiethylammonio) propyloxy]psoralen bromide.

10. The psoralen compound of claim 5 wherein a bromine is attached to the carbon at position 3 or position 5 of the structure.

* * * * *

UNITED STATES PATENT AND TRADEMARK OFFICE
CERTIFICATE OF CORRECTION

PATENT NO. : 5,919,935
DATED : July 6, 1999
INVENTOR(S) : Matthew S. Platz, Tongqian Chen, Shashi S. Kagan
Helena M. Pereira It is certified that error appears in the above-indentified patent and that said Letters Patent is hereby corrected as shown below:

In the Abstract, in the second line after the formula please delete "quartemary" and replace with -- quarternary --.

In claim 1, line 53 please delete "quartemary" and replace with -- quarternary --.

Signed and Sealed this

Twenty-third Day of November, 1999

Attest:

Q. TODD DICKINSON

*Attesting Officer*  *Acting Commissioner of Patents and Trademarks*